United States Patent [19]

MacDonald

[11] Patent Number: 5,174,807
[45] Date of Patent: Dec. 29, 1992

[54] PLANT ERADICATION METHOD

[76] Inventor: Christopher N. MacDonald, P.O. Box 240, Kailua, Hi. 96734

[21] Appl. No.: 670,318

[22] Filed: Mar. 15, 1991

[51] Int. Cl.⁵ .............................................. A01N 57/04
[52] U.S. Cl. ............................................ 71/86; 71/65; 71/DIG. 1; 47/58; 124/72; 273/418
[58] Field of Search .................... 71/65, 86, DIG. 1

[56] References Cited

U.S. PATENT DOCUMENTS

| | | | |
|---|---|---|---|
| 3,369,609 | 2/1968 | Fogelgren | 169/31 |
| 3,417,719 | 12/1968 | Nitenson | 114/20 |
| 3,689,661 | 9/1972 | Braude et al. | 71/65 |
| 3,695,246 | 10/1972 | Filippi | 124/11 |
| 3,938,272 | 2/1976 | Ditto | 42/55 |
| 3,989,027 | 11/1976 | Kahelin | 124/58 |
| 4,134,228 | 1/1979 | Ortiz | 46/88 |
| 4,147,152 | 4/1979 | Fischer | 124/76 |
| 4,432,768 | 2/1984 | Brown | 601/200 |
| 4,531,503 | 7/1985 | Shepherd | 124/76 |
| 4,819,609 | 4/1989 | Tippmann | 124/72 |
| 4,936,282 | 6/1990 | Dobbins | 124/74 |

OTHER PUBLICATIONS

Grays Manual of Botany, 8th Ed., p. 555.
CA:87:79494s "Herbicidal treatments for control of *Cannabis sativa*", Horowitz, Bull. Narc. 1977, 29(1) 75–84.

Primary Examiner—Richard L. Raymond
Assistant Examiner—B. Bembenick
Attorney, Agent, or Firm—Fulwider, Patton, Lee & Utecht

[57] ABSTRACT

A method of eradicating plants on an inaccessible terrain by selecting hollow balls formed by a frangible membrane, filling such balls with respective charges of herbicide fluid of the type to which such plants are susceptible to provide a supply of such charged balls. Selecting a repeater ball firing gun of the type incorporating a mechanism having sufficient propulsion to transmit a certain minimum muzzle velocity to such balls in a repetitive manner, transporting such gun by helicopter to hover over such terrain. Shooting a quantity of such balls at each plant from a range sufficiently close to cause the skins of such balls to be ruptured upon impact to thereby splash herbicide on the respective plants.

15 Claims, 2 Drawing Sheets

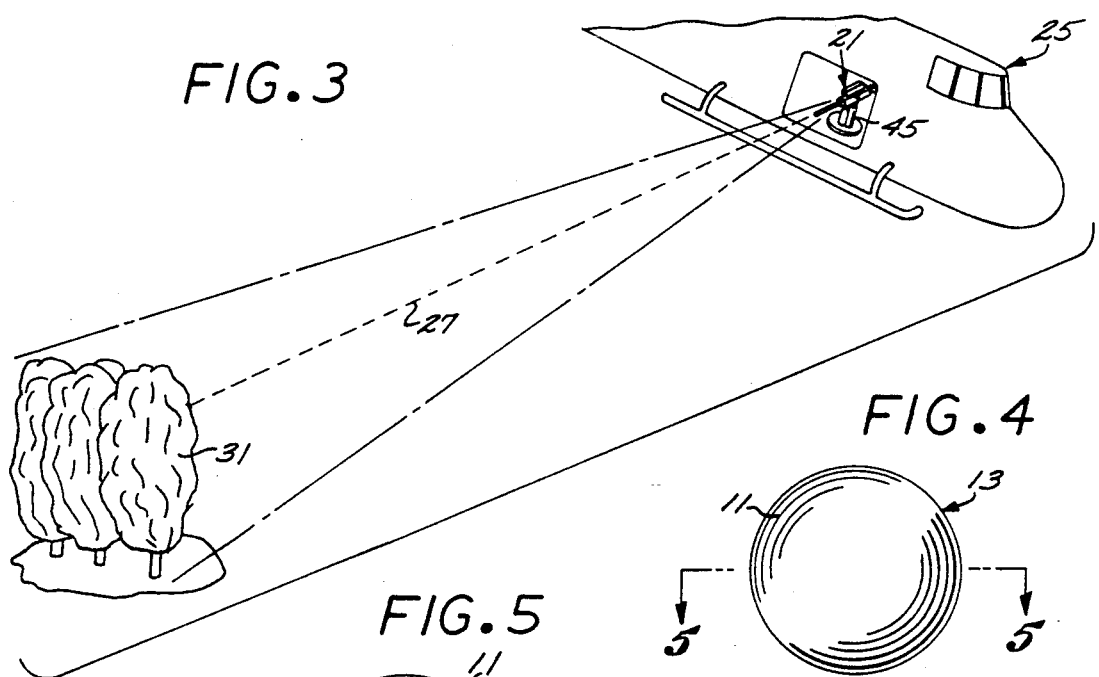
FIG.3
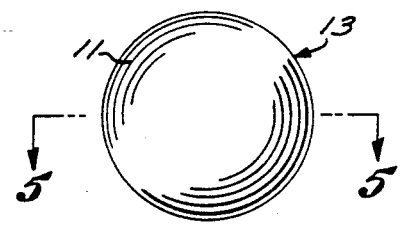
FIG.4
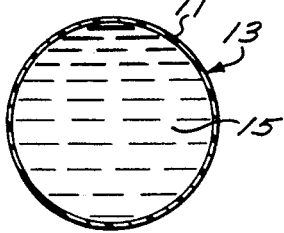
FIG.5
FIG.6
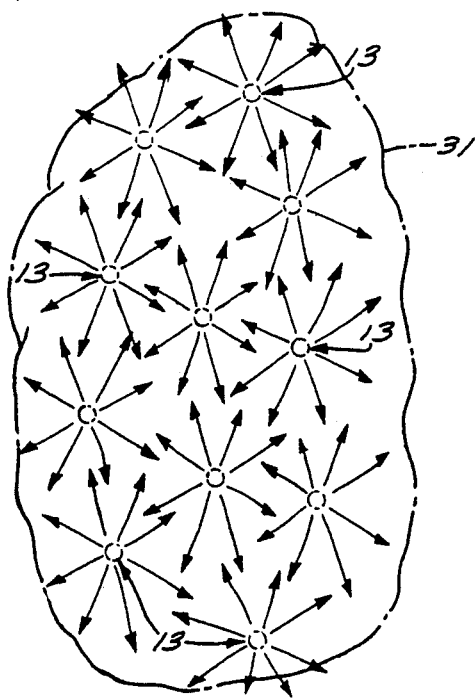
FIG.7
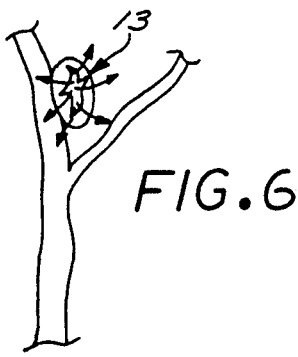
FIG.8
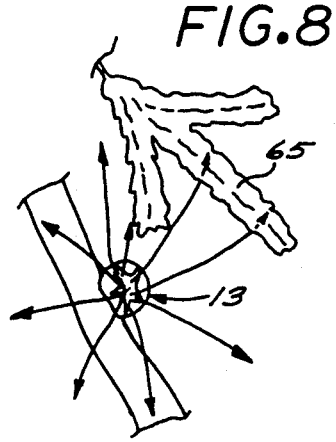

PLANT ERADICATION METHOD

BACKGROUND OF THE INVENTION

1. Field of the Invention:

The present invention relates to a method of eradicating unwanted vegetation, such as marijuana plants, located in a remote or relatively inaccessible area.

2. Description of the Prior Art:

Drug producing plants, such as marijuana plants, have gained prominence as a source of drugs which might be exploited as a lucrative source of illegal income. Efforts by law enforcement agencies to discourage or limit the cultivation and harvesting of such illegal plants have led to the proposal of numerous different methods of eradication.

Because of the difficulty of gaining access to such remote locations, national forests and reserves have become particularly popular as locations for the planting and cultivation of such illegal plants.

One method employed to eradicate illegal vegetation in locals where the terrain is relatively inaccessible is the deployment to the locale of a number of drug enforcement agents who then manually attack the crop in a laborious and time consuming manner by severing each plant one by one, transporting the severed plants to a centralized location and destroying said plants.

Another conventional approach, particularly for plants in relatively inaccessible areas, has been to first send out spotter personnel in a spotter helicopter for the purpose of spotting illicit plants for subsequent eradication. Once located, the coordinates of the spotting are recorded and upon returning to base, an eradication team is typically sent out by a transport helicopter to hover over the spotted area to permit the team to rappel thereinto for the purpose of either prematurely harvesting and burning the crop or applying herbicides thereto. This approach has proven relatively inefficient and time consuming thus imposing an excessive burden on the tax payers and unduly drawing from the available work force.

Other approaches long relied upon in endeavoring to eradicate such remotely located crops has been to actually transport a storage tank of herbicide in a helicopter directed to a hovering position typically elevated some 100' or more over the terrain on which the crop is growing. Typically the apparatus utilized for application of the herbicide is somewhat unsophisticated, often involving nothing more than a length of hose suspending a shower head type nozzle to the general proximity of the offending plants in hopes that the nozzle head can be positioned over the target plant. This approach suffers the shortcoming that the liquid herbicide can sometimes coagulate in the nozzle. Additionally, the dangling nozzle head is blown and swayed under the influence of various undulations of the hose brought about by the helicopter rotor down wash, helicopter movement and general wind currents. Experience has proven that the pendulum action of the hose and nozzle itself results in imprecise focusing of the herbicide spray thus resulting in the nozzle head frequently passing back and forth over the top of and to the sides of the target plants thus spraying a relatively large area surrounding the plant thus consuming an unwarranted volume of herbicide leading to waste and possible contamination of the surrounding vegetation. Moreover, the dwell time for the helicopter hovering over the crop of plants is considerable due to the fact that, unless the entire area is to be broadcast sprayed, each plant must be dealt with individually and for a sufficient time to assure that the swinging nozzle head treats both the leaf surface to such an extent that some penetration is provided to the vulnerable underside of the plant leaves. Due to the expense of helicopter operation, this then is not only a tedious but an expensive task.

Thus, there exists a need for an effective system for delivering measured quantities of herbicide at relatively precise locations on the target plants to be eradicated to thereby provide for effective delivery in precise quantities at pinpointed locations on offending plants on a remote and difficult terrain.

The present invention contemplates the use of a pressurized gun to impel frangible herbicide charged balls from a vehicle such as a helicopter to impact the stems or branches of a plant to cause the balls to burst, thus splashing the herbicide on the leaves of the plants.

Pressurized guns and frangible balls containing colored liquid paint have long been known for use in entertainment games wherein contestants shoot the balls at a velocity which will, while avoiding impact on the person of a competitor with sufficient force to cause undue pain or injury, will cause the ball skin to burst to splash the contained paint on the person thus creating a mark to identify the loser of the contest. The method of using such guns is not, however, satisfactory for eradicating offending plants from a remote distance, as from a helicopter platform, since the paint utilized would not be toxic to the plant and the muzzle velocity of such guns is insufficient to impart sufficient velocity to the frangible balls to propel them accurately through the down wash from the helicopter rotor on a sufficiently accurate flight path to strike the plant with a sufficient degree of precision to be practical.

Moreover, the skin membrane of such paint balls is typically without sufficient strength to withstand the relatively high muzzle velocities which must be imparted to the herbicide balls for the desired accuracy and impact forces necessary to assure bursting of the skin membrane upon impact.

It has also been known to utilize a pressurized gun to deliver a marker pellet to be used as a marker for marking the trunks of trees to be thinned from a forest. These guns are, however, typically intended for close range application thus requiring only low muzzle velocity and the pellets typically employ membrane skin which bursts under relatively modest forces substantially less than the comparatively high forces imposed by the high muzzle velocities necessary for proper operation of the herbicide charged balls of my invention.

SUMMARY OF THE INVENTION

The present invention is characterized by the selection of frangible spherical ball skins, filling such ball skins with charges of herbicide, mounting a repeating pressure gun on a vehicle and transporting such vehicle to a site of offending plants. Then, while holding the transport vehicle relatively stationary, the balls are shot from the muzzle of the gun at a sufficiently close range and with sufficient velocity to cause the air borne balls to be directed onto the stems of the offending plants to cause the skins thereof to burst and the contained herbicide to splash onto the plants and about the leaves thereof.

Other objects and features of the invention will become apparent from consideration of the following description taken in connection with the accompanying drawings.

BRIEF DESCRIPTION OF THE DRAWINGS

FIG. 3 is a perspective view of a transport vehicle, in a reduced scale, mounting the gun of FIG. 1 for shooting the herbicide balls at offending plants;

FIG. 4 is a front elevational view of an herbicide containing ball utilized in the method of the present invention;

FIG. 5 is a horizontal sectional view taken along the line 5—5 of FIG. 4;

FIG. 6 is a elevational view, in reduced scale, of the ball shown in FIG. 4 as it strikes the stem of an offending plant;

FIG. 7 is a diagrammatic view of a number of herbicide containing balls fragmenting upon impact; and FIG. 8 is an elevational view, in reduced scale, of an herbicide charged ball, of the type shown in FIG. 4, depicted impacting the stem of a plant.

DETAILED DESCRIPTION OF THE PREFERRED EMBODIMENT

Figure 2:
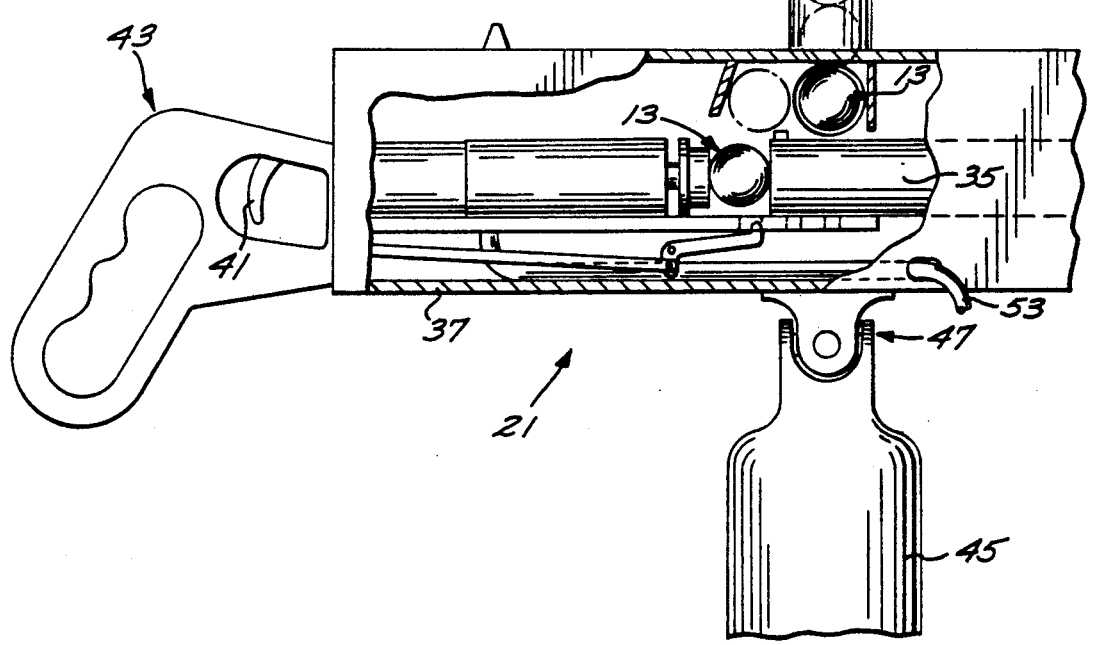
FIG. 2 is a vertical sectional view, in enlarged scale, taken along the lines 2—2 of FIG. 1.

Referring to FIGS. 2, 3 and 5, the method of the present invention involves selecting a skin 11 for a hollow ball, generally designated 13, filling such skin with a liquid compound 15 incorporating a dye and a sticking agent, and storing a supply of the charged balls in a magazine 19 for discharge via a pressurized gun, generally designed 21. The gun 21 is typically mounted on the floor of a transport helicopter 25 such that the gun may be actuated to drive the balls along a pathway 27, projecting through the down wash of the helicopter rotor and onto the stems of illegal vegetation which may be in the form of marijuana plants 31. The muzzle velocity of the balls 13 from the gun 21 is sufficient that, at the distance of delivery, the skin 11 of the ball will burst thus causing the herbicide 15 to splash onto the stems and leaves of the plant thereby entering the vascular system of such leaves and poisoning the plant.

I have determined that a ball skin 11 made from a commercially available gelatin, sold under the trade designation California Magnum by Banner Gelatin Products, Chatsworth, Calif. and having a thickness of between 0.015 and 0.020 inches is satisfactory for the present invention. It is important that the strength of the skin be sufficient to withstand the high forces imparted thereto upon propulsion from the muzzle of the gun at a velocity of at least 380 feet per second but yet be sufficiently frangible to burst upon impact with the stem of a branch of a targeted plant.

A convenient, economical and effective method of eradicating illegal vegetation has long been sought by governmental agencies, such as the Drug Enforcement Administration (DEA). Such efforts have generally focused on the destruction of such vegetation by manual harvesting thereof, manual applications of herbicides or dispensing of herbicides through a nozzle dangled on the end of a hose suspended from a helicopter. Until the present invention, there had been no practical method of delivering encapsulated herbicide with precision and efficiency to thereby minimize consumption of the herbicide and damage to vegetation surrounding the target vegetation.

I have discovered by that by encapsulating herbicide in a gelatin skin 11 having sufficient strength to withstand muzzle velocities imparted by the gun 21 on the order of 380 to 450 feet per second, and shooting such balls from the gun in muzzle velocities of over 380 feet per second, the balls may be efficiently and effectively delivered with acceptable accuracy over distances on the order of 100 to 150 feet or more to thereby provide for efficient and effective application of herbicide.

In my preferred embodiment, I utilize a conventional pressure gun 21 available from Tippmann Pneumatics of Fort Wayne, Ind. under Model No. 68 Special. The gun is semiautomatic, firing over 300 rounds per minute and has been modified to raise the muzzle velocity from about 300 feet per second to between 380 and 450 feet per second.

The herbicide 15 is preferably a liquid formulation sold under the trade name ROUNDUP by Monsanto and packaged in the gelatin capsule by Banner Gelatin Products of Chatsworth, Calif.

Figure 1:
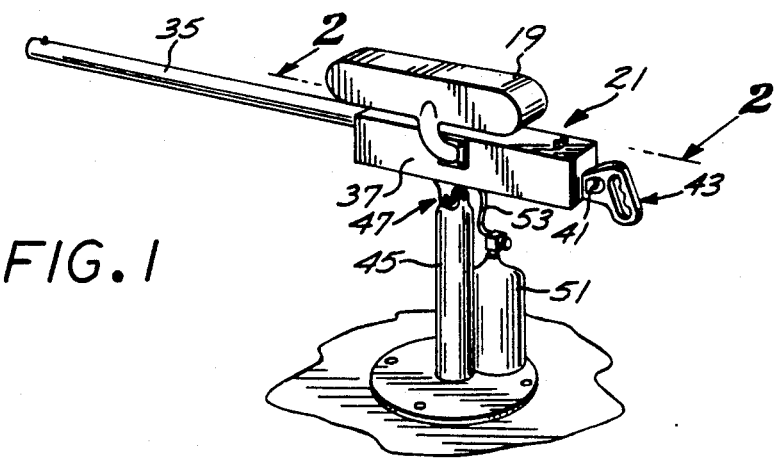
FIG. 1 is a perspective view of a pressurized gun which may be utilized in the herbicide ball delivery method of the present invention.

It will be appreciated that the gun 21 incorporates the usual barrel 35 (FIG. 2) mounted within a housing 37 for sequential receipt of herbicide filled balls 13 from the magazine 19. Actuation thereof is controlled by a trigger 41 mounted in a pistol grip assembly, generally designated 43. The gun is mounted on the helicopter floor by means of a pedestal 45 incorporating a gimbal or universal joint, generally designated 47, and incorporating an internal to the pedestal $CO_2$ pressurization tank 51. Pressure to the gun is then supplied from a pressure tank 51 (FIG. 1) connected thereto by means of a supply conduit 53.

In operation, the balls 13 will be manufactured by filling the skins 11 with the herbicide fluid 15 to provide the ball diameter corresponding with the 68 caliber barrel 35 of the gun 21. The balls may then be stored ready for usage when the occasion arises.

When a crop of illegal vegetation, such as the marijuana plants 31 shown in FIG. 3, are spotted, the spotting helicopter 25 mounting the gun 21 will be positioned such that the operator may fire the gun at the target site. A supply of balls 13 will be carried on board and the magazine 19 filled in preparation for application of the herbicide. The helicopter 25 will be moved into hovering position over the target and the gun operator will aim the gun 21 at the plants 31. By then pulling the trigger 41, the balls will be discharged at a rate of about 300 per minute. I have discovered that with the ball construction described therein, the fail rate of such balls, even at muzzle velocities of 380 feet per second and above, is less than 2% thus providing for only minimal loss of herbicide in the gun mechanism itself and providing for efficient delivery along the flight path 27 to the plants 31.

Upon impact of the balls 13 with the plant stems and branches as depicted in FIGS. 6 and 8, sufficient impact forces will be generated to rupture the skin 11 thereby abruptly ejecting the charge of herbicide 15 therein to splash on the surface of the plants itself. It is important that the balls 13 penetrate the foliage of the plants to impact on the stems such that the herbicide splashes upwardly to the vulnerable underside of the marijuana leaves 65 (FIG. 8) to thus enter the pores thereof and migrate through the plant vasculature system. Typically approximately six to eight balls are impacted upon each plant 31 to thus assure effective distribution of the herbicide to assure complete eradication of the plants. It will be appreciated that with a delivery rate of 300 balls per minute, a great number of plants may be treated in a relatively small period of time. Furthermore, with the precision afforded by the relatively high velocity at which the balls are impelled toward the plants, accuracy of the trajectory is assured thus enhancing the efficiency of application and minimizing herbicide application to surrounding vegetation.

From the foregoing, it will be appreciated that the method of the present invention provides an economical, convenient and effective means for application of herbicide to illegal vegetation without risk to the workmen involved.

Various modifications and changes may be made with regard to the foregoing detailed description without departing from the spirit of the invention.

What is claimed is:

1. A method for the precision application of measured amounts of foliar-acting herbicide to marijuana plants, including the following steps:
   selecting an herbicide of the type to which such marijuana plants are susceptible;
   selecting a supply of hollow balls formed by frangible skins;
   filling said balls with predetermined charges of such herbicide to form charged balls;
   selecting a repeating powered gun for shooting said balls from said supply, said gun being of the type having a propulsion mechanism adapted to repetitively deliver a selected propulsion force to said charged balls sufficient to generate a muzzle velocity of at least about 380 feet per second;
   said balls being selected with skins having sufficient strength to, when charged with said charges of herbicide, upon application of said selected propulsion force, resist breaking but to, upon striking the stems of such plants with a predetermined velocity, burst;
   transporting said gun and supply of charged balls to the proximity of said plants;
   aiming said gun sequentially at different ones of said plants from a selected distance sufficient to cause said balls to, when fired from said gun, be propelled along a projectile path to the respective targeted plants to impact said stems with said predetermined velocity; and
   firing a selected portion of said supply of balls at each plant to be eradicated causing said balls to penetrate at least some of the respective foliage of the targeted plants striking such stems thereof to burst said skins causing said herbicide to splash on said stems and the underside of the leaves thereof to enhance foliar absorption of such herbicide.

2. A method as set forth in claim 1 wherein: said distance is selected to be between 100 and 150 feet.

3. A method as set forth in claim 1 adapted for eradicating plants including stems carrying foliage therefrom and that includes the step of:
   charging said balls with a liquid mixture of said herbicide and a dye;
   selecting said gun with sufficient muzzle velocity to, when shooting said balls from said selected distance, cause them to penetrate at least some of said foliage to strike the respective stems to burst said skins and splash said mixture on said stems and foliage to, in addition to applying said herbicide, apply said dye to mark the spots treated by said herbicide.

4. A method as set forth in claim 1 wherein:
   said balls are selected as 68 caliber in size; and
   said gun is selected for shooting 68 caliber balls.

5. A method of eradicating plants as set forth in claim 1 that includes:
   said step of transporting said gun and supply of charged balls includes the selection of and transport by helicopter.

6. A method of eradicating plants as set forth in claim 1 wherein:
   said selection of said balls includes the step of selecting said balls with a skin construction of gelatin having a thickness of at least 0.015 inch.

7. A method as set forth in claim 1 wherein:
   said gun is selected to deliver substantially 300 balls per minute.

8. A method as set forth in claim 1 wherein:
   said selected distance is selected to be between 100 and 150 feet.

9. A method as set forth in claim 1 wherein:
   said selected distance is selected to be at least 100 feet.

10. A method as set forth in claim 1 that includes the step of:
    operating said gun to impact at least six balls on each such targeted plant.

11. A method as set forth in claim 1 wherein:
    said balls are selected with gelatin skins having a thickness of between 0.015 and 0.020 inches.

12. A method as set forth in claim 1 wherein:
    said gun is selected to establish said muzzle velocity at between 380 and 450 feet per second.

13. A method as set forth in claim 1 for targeting of marijuana plants and wherein:
    said step of selecting herbicide includes the selection of glyphosate.

14. A method as set forth in claim 3 wherein:
    the selection of said mixture includes the step of selecting it with a sticking agent to cause the mixture to stick to the area of such plants targeted with said charged balls.

15. A method of precisely applying measured amounts of herbicide to marijuana plants having foliage thereon, including the following steps:
    selecting a foliar-acting herbicide to which said marijuana plants are susceptible;
    selecting hollow balls constructed of skin frangible at a predetermined bursting force and formed of a predetermined outside diameter;
    charging said balls with measured charges of said herbicide to provide charged balls each having a predetermined weight;
    selecting a gun for shooting said charged balls at a predetermined muzzle velocity;
    transporting said gun and charged balls to the proximity of such plants to be treated;
    mounting said gun in a helicopter to hover over said plants at a predetermined distance therefrom;
    aiming said gun sequentially at targeted plants;
    firing a selected number of charged balls at said plants;
    said skin of said balls being of material selected with sufficient strength to withstand the forces of said muzzle velocity and said predetermined distance being selected to cause said balls to, when fired from said predetermined distance at said predetermined muzzle velocity, penetrate at least some of such foliage and impact on the stems thereof with sufficient velocity to apply said predetermined bursting force to the respective skins thereof to cause the respective ball skins to burst and splash at least part of said measured quantities of said selected herbicide on the bottom side of said foliage to enhance systemic absorption of said charges of herbicide.

* * * * *